United States Patent [19]

Bender

[11] 4,263,311
[45] Apr. 21, 1981

[54] 5,6-PHENYL-2,3-DIHYDROIMIDAZO [2,1-b] THIAZOLES

[75] Inventor: Paul E. Bender, Willingboro, N.J.

[73] Assignee: SmithKline Corporation, Philadelphia, Pa.

[21] Appl. No.: 825,612

[22] Filed: Aug. 18, 1977

Related U.S. Application Data

[63] Continuation-in-part of Ser. No. 727,184, Sep. 27, 1976, abandoned.

[51] Int. Cl.³ .......................................... C07D 277/60
[52] U.S. Cl. ...................................... 424/270; 548/154
[58] Field of Search ...................... 260/306.7 T, 301; 424/270, 546; 548/154

[56] References Cited

U.S. PATENT DOCUMENTS

| 2,969,369 | 1/1961 | Krimmel | 260/306.7 |
| 3,267,112 | 8/1966 | Iwai | 260/305 |
| 3,274,209 | 9/1966 | Raeymaekeus | 260/306.7 |
| 3,455,924 | 7/1969 | Lednicer | 260/256.4 |
| 3,732,215 | 5/1973 | Hawgwitz | 260/243 R |
| 3,895,021 | 7/1975 | Weinstock | 260/306.8 R |
| 3,932,395 | 1/1976 | Hideg | 260/243 R |
| 4,059,588 | 11/1977 | Baklien | 260/306.7 T |
| 4,110,460 | 8/1978 | Baetz | 424/270 |

FOREIGN PATENT DOCUMENTS

| 7417111 | 5/1974 | France | 260/306.7 T |
| 1180202 | 2/1970 | United Kingdom | 260/306.7 T |

OTHER PUBLICATIONS

Mazur, A. I. et al., Chemical Abstracts, 72:12645P (1970), Abstract from Khim.-Favm. Zh. 3(8) 11-15 (1969).

Burger, A., "Medincinal Chemistry", 2nd ed., Interscience Publishers, Ltd., London, 1963, p. 42.

Primary Examiner—Nicholas S. Rizzo
Attorney, Agent, or Firm—Joan S. Keps; Richard D. Foggio; Alan D. Lourie

[57] ABSTRACT

The compounds are 5,6-phenyl-2,3-dihydroimidazo[2,1-b]thiazoles which have antiarthritic activity. A preferred compound is 5,6-bis(p-anisyl)-2,3-dihydroimidazo[2,1-b]thiazole.

6 Claims, No Drawings

5,6-PHENYL-2,3-DIHYDROIMIDAZO [2,1b] THIAZOLES

This application is a continuation-in-part of Ser. No. 727,184 filed Sept. 27, 1976, now abandoned.

This invention relates to new 2,3-dihydroimidazo[2,1-b]thiazoles having, in the 5 and 6 positions, phenyl groups at least one of which is substituted. These compounds have antiarthritic activity and are particularly of use in the treatment of rheumatoid arthritis.

The compounds of this invention are represented by the following formula:

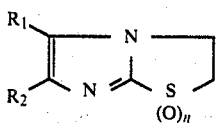
FORMULA I in which:

$R_1$ and $R_2$, being the same or different, are phenyl optionally substituted by lower alkoxy, lower alkyl, lower alkylthio, lower alkylsulfinyl, chloro, fluoro, bromo, 2,2,2-trifluoroethoxy, allyloxy, hydroxy, lower alkanoyloxy, 3,4-methylenedioxy, trifluoromethyl, amino, N-lower alkanoylamino, di-N,N-lower alkylamino, N-lower alkanoyl-N-lower alkylamino, 4-lower alkoxy-3-halo or 4-lower alkoxy-3-lower alkyl, at least one of $R_1$ and $R_2$ being said substituted phenyl, or one of $R_1$ and $R_2$ is 3,4-di-lower alkoxyphenyl, and n is 0, 1 or 2, or a pharmaceutically acceptable acid addition salt thereof.

Particular compounds of this invention are represented by Formula I in which $R_1$ and $R_2$ are lower alkoxyphenyl and in which the lower alkoxy groups are each in the para position.

As advantageous compound of this invention is the compound of Formula I in which $R_1$ and $R_2$ are p-methoxyphenyl, said compound being 5,6-bis(p-anisyl)-2,3-dihydroimidazo[2,1-b]thiazole.

Other advantageous compounds of this invention are compounds of Formula I in which $R_1$ and $R_2$ are both p-ethoxyphenyl, p-fluorophenyl or p-methylthiophenyl. Also, compounds of Formula I in which n is 0 or 1 are preferred, particularly when $R_1$ and $R_2$ are the advantageous substituted phenyl groups indicated hereabove.

The compounds of this invention are prepared by the following procedures:

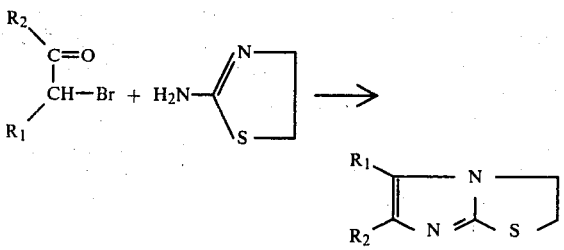

According to the above procedure, an α-bromodesoxybenzoin is reacted with 2-amino-4,5-dihydrothiazole. The reaction is preferably carried out in an anhydrous polar organic solvent, such as acetonitrile or dimethylformamide or a lower alkanol such as methanol or a mixture thereof, preferably carried out in acetonitrile or dimethylformamide, at room temperature in the presence of an added base such as potassium carbonate or triethylamine.

Alternatively, compounds of this invention are prepared by alkylation of a 4,5-diphenyl-2-mercaptoimidazole with an ethylene-1,2-dihalide in dimethylformamide or other polar solvent, preferably at reflux temperature and in the presence of a poorly nucleophilic base as potassium carbonate or alternatively at about room temperature in the presence of potassium hydride. The required 4,5-diphenyl-2-mercaptoimidazoles are prepared by condensing a benzoin with thiourea in a high boiling polar solvent such as dimethylformamide or hexanol similar to the procedure described by P. M. Kochergin, *Zhur. Obshchei Khim.*, 31:1093 (1961), *Chem. Abstr.*, 55:23503f. Compounds of this invention in which the phenyl substitute in $R_1$ or $R_2$ is lower alkylthio, lower alkylsulfinyl, N-lower alkanoylamino, 3,4-methylenedioxy, 4-lower alkoxy-3-halo or 4-lower alkoxy-3-lower alkyl are prepared by this alternate procedure.

The sulfoxide compounds, that is the compounds of Formula I in which n is 1, are prepared by oxidation of the 5,6-diphenyl-2,3-dihydroimidazo[2,1-b]thiazoles, preferably with sodium periodate, in aqueous methanol-methylene chloride according to the proceure of N. J. Leonard and C. R. Johnson, *J. Org. Chem.*, 27:282 (1962), or with one equivalent or either hydrogen peroxide or an organic peracid such as meta-chloroperbenzoic acid.

The sulfone compounds, that is the compounds of Formula I in which n is 2, are obtained by oxidation of the corresponding 5,6-diphenyl-2,3-dihydroimidazo[2,1-b]thiazoles or their sulfoxide derivative with excess meta-chloroperbenzoic acid in a halogenated solvent or with excess 30% hydrogen peroxide in acetone.

Alternatively, the sulfoxide and sulfone compounds are prepared by oxidation of the 2-amino-4,5-dihydrothiazoles, using the oxidizing agents indicated above, to give S-oxide and S-dioxide compounds and then reaction with the α-bromodesoxybenzoins.

Other methods of preparation which may be preferable for certain of the compounds of this invention are illustrated in the examples. For example, the hydroxyphenyl compounds may be prepared by demethylation of the corresponding methoxyphenyl compounds.

Certain of the compounds of Formula I are conveniently prepared from other compounds of Formula I. The lower alkanoyloxy and the allyloxy phenyl compounds are prepared by acylating or alkylating the corresponding hydroxyphenyl compounds. The aminophenyl compounds are prepared by hydrolysis of the lower alkenoylaminophenyl compounds. The N-lower alkanoyl-N-lower alkylaminophenyl compounds are prepared by alkylating the N-lower alkanoylaminophenyl compounds and the N,N-di-lower alkylaminophenyl compounds are prepared by hydrolysis of the N-lower alkanoyl-N-lower alkylaminophenyl compounds followed by alkylation of the resulting N-lower alkylaminophenyl compounds.

The pharmaceutically acceptable acid addition salts of the compounds of Formula I are formed with strong or moderately strong organic or inorganic acids by methods known to the art. For example, the base is reacted with an organic or inorganic acid in aqueous miscible solvent, such as ethanol, with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

The α-bromodexoxybenzoin starting materials in the process described above are known to the art or are prepared by bromination of the desoxybenzoins. The desoxybenzoins are known to the art or are prepared, for example, by reacting a substituted benzonitrile with a substituted benzyl magnesium chloride. Also, desoxybenzoins may be prepared by reduction of benzoins, for example, using tin and hydrochloric acid. Methods for the preparation of benzoins and desoxybenzoins are well known to the art, see for example "Organic Reactions", Vol. IV, Chapter 5 "The Synthesis of Benzoins" (John Wiley & Sons, Inc., New York, 1948).

The compounds of this invention are useful in treatment of arthritis. This activity is demonstrated by the following test procedures.

Inhibition of adjuvant induced polyarthritis in rats, as measured by reduction of rat paw edema, is produced by compounds of this invention at daily doses of about 12.5-100 mg./kg. orally. In this test procedure, adjuvants arthritis in rats is produced by a single intradermal injection of 0.75 mg. of *Mycobacterium butyricum* suspended in white paraffin oil into the left hindpaw footpad. The injected paw becomes inflammed (increased volume) and reaches maximal size within three to five days (primary lesion). The animals exhibit a decrease in body weight gain during the initial period. The adjuvant arthritis (secondary lesion) occurs after approximately ten days and is characterized by inflammation of the non-injected right hind leg, decrease in body weight, and further increase in the volume of the injected left hind leg. Test compounds are administered daily, beginning on the day of the adjuvant injection, for 17 days thereafter, exclusive of days 4, 5, 11 and 12. Antiarthritic activity is shown by the ability to protect the animals against the development of both primary and secondary lesions of adjuvant arthritis.

In the carrageenan induced rat paw edema test, anti-inflammatory activity is produced by the compounds of this invention at doses of about 25-100 mg./kg. orally.

In addition, compounds which have immunoregulatory activity provide benefit for treatment of rheumatoid arthritis. Stiller et al., *Annals of Internal Medicine* 82:405-410 (1975), Froland et al., *Scandinavian J. Immunol.* 3:223-228 (1974) and *The Lancet*, Jan. 11, 1975, page 111. It has been found that compounds of this invention, particularly a preferred compound of this invention, 5,6-bis(p-anisyl)-2,3-dihydroimidazo[2,1-b]thiazole, demonstrate the ability to regulate cell-mediated immunity as shown in procedures such as the oxazolone-induced contact sensitivity test procedure in which mouse paw is measured. This procedure is described by Griswold et al., *Cellular Immunology* 11:198-204 (1974). In contrast to anti-inflammatory agents, such as indomethacin, and immunosuppressive agents, such as methotrexate and cyclophosphamide, both of which inhibit the oxazolone-induced response, this preferred compound at doses of from about 12.5 to 100 mg./kg., orally, not only does not inhibit but enhances the oxazolone-induced response.

Because of the pharmacological profile of this preferred compound, that is the anti-inflammatory, antiarthritic and immunoregulatory activity, it is expected that this compound would share the activity in man of the nonsteroidal anti-inflammatory agents (aspirin), remission inducing drugs (gold sodium thiomalate) and immunomodulators (levamisole).

In addition to having utility in rheumatoid arthritis, immunoregulatory agents have potential utility in other diseases where cell mediated immunity is compromised. Examples of such diseases are systemic lupus erythematosus and autoimmune thyroiditis (Stiller et al. cited hereabove). Also, diseases such as atopic dermatitis, recurrent aphthus ulceration, recurrent upper respiratory tract infections in children and flu, lung and breast cancer, transient granulocyclopenia and allergic skin reactions have been successfully treated with levamisole which is an agent which restores impaired cell mediated immune responses [Symoens et al, *Journal of the Reticuloendothelial Society*, 21:175-221 (1977)].

Some of the compounds of this invention, for example those compounds of Formula I in which $R_1$ and $R_2$ are both o-methoxyphenyl (o-anisyl), m-methoxyphenyl (m-anisyl), p-butoxyphenyl, p-tolyl, p-trifluoromethylphenyl or p-acetamidophenyl demonstrate, principally, activity in the test for immunoregulatory activity, that is they enhance oxazolone-induced response. Other of the compounds of this invention, for example those in which $R_1$ and $R_2$ are both p-chlorophenyl or 3,4-methylenedioxyphenyl, demonstrate, principally, activity in the test for inhibition of adjuvant induced polyarthritis in rats. In addition, other compounds such as the preferred compound, 5,6-bis-(p-anisyl)-2,3-dihydroimidazo[2,1-b]-thiazole, demonstrate activity in both of these test procedures and also in the carrageenan induced rat paw edema test. Also, the compounds of Formula I in which $R_1$ and $R_2$ are both p-ethoxyphenyl, p-fluorophenyl or p-methylthiophenyl demonstrate activity in both the adjuvant induced polyarthritis and the oxazolone test procedures. Although all of these compounds are useful in the treatment of arthritis, compounds having activity in both tests are particularly advantageous in treatment of arthritis.

The compounds of this invention are administered in conventional dosage forms prepared by combining a compound of Formula I in an amount sufficient to produce antiarthritic activity with standard pharmaceutical carriers according to conventional procedures. These procedures may involve mixing, granulating and compressing or dissolving the ingredients as appropriate to the desired preparation. The resulting pharmaceutical compositions are also objects of this invention.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or nonaqueous liquid suspension.

To obtain a stable water soluble dose form, a pharmaceutically acceptable acid addition salt, preferably sulfate, of a compound of formula I is dissolved in an aqueous solution of an organic or inorganic acid, such as a 0.3 M solution of succinic acid or, preferably, citric acid. In addition to sulfate, exemplary of other water soluble salts are methanesulfonate, phosphate and hydrochloride.

Preferably, each dosage unit will contain the active ingredient in an amount of from about 25 mg. to about 200 mg.

The method of producing antiarthritic activity by administering internally to an animal a compound of Formula I is also an object of this invention. The compound of Formula I is administered in an amount sufficient to produce antiarthritic activity. The route of administration may be orally or parenterally. The daily dosage regimen will be preferably from about 75 mg. to about 600 mg. When the method is carried out as described above, antiarthritic activity is produced.

One skilled in the art will recognize that in determining the amounts of the active ingredient in the claimed compositions and used in the claimed methods, the activity of the chemical ingredient as well as the size of the host animal must be considered.

The terms "lower alkyl" and "lower alkoxy" where used herein denote groups having preferably 1–4 carbon atoms.

The following examples are not limiting but are illustrative of the invention.

EXAMPLE 1

(a) Desoxy-p-anisoin (180 g.) was suspended in 1 liter of benzene (previously dried by distilling off 400 ml. from 1400 ml.). Bromine (113 g.) was added over 15 minutes. The reaction mixture was then flushed with nitrogen for 15 minutes and evaporated in vacuo. The residue was recrystallized with 100 ml. of methylene chloride and 200 ml. of ether to give α-bromodesoxy-p-anisoin.

(b) 2-Amino-4,5-dihydrothiazole (10.2 g.) in 50 ml. of methanol was added to a stirred solution of 33.5 g. of α-bromodesoxy-p-anisoin in 200 ml. of acetonitrile in a nitrogen atmosphere. After 2–3 days at room temperature, the solution was evaporated in vacuo. The residue was partitioned between 200 ml. of methylene chloride and 10% aqueous sodium carbonate solution. The organic solution was washed twice with saturated aqueous sodium chloride solution, dried over sodium sulfate, filtered and evaporated in vacuo. The residue was recrystallized twice from acetonitrile to give 5,6-bis(p-anisyl)-2,3-dihydroimidazo[2,1-b]thiazole, m.p. 154.5°–156.5° C.

To a solution of the above prepared base in 3 parts methylene chloride and 1 part absolute ethanol was added an equimolar amount of hydrogen bromide in absolute ethanol. The mixture was stripped of solvent and the residue recrystallized from 95% ethanol containing a small amount of 48% hydrogen bromide to give 5,6-bis(p-anisyl)-2,3-dihydroimidazo[2,1-b]thiazole hydrobromide, m.p. 205° C.

Alternatively and preferably, 5,6-bis(p-anisyl)-2,3-dihydroimidazo[2,1-b]thiazole is prepared by the following procedure.

(c) A suspension of 145 g. (0.433 mole) of α-bromodesoxy-p-anisoin, 88.36 g. (0.865 mole) of finely powdered 2-amino-4,5-dihydrothiazole and 179.5 g. (1.3 moles) of pulverized potassium carbonate in 1.0 liter of sieve dried acetonitrile under nitrogen was stirred at 25° C. for 3 days. The solvent was evaporated in vacuo and the residue treated with methylene chloride and 5% aqueous sodium carbonate. The organic phase was removed, washed once with 10% aqueous sodium carbonate, 3 times with water, dried over potassium carbonate, filtered and evaporated in vacuo. A solution of the residue dissolved in methylene chloride was treated with charcoal, filtered and hexane added. The precipitate was filtered and recrystallized from methylene chloride to give 5,6-bis(p-anisyl)-2,3-dihydroimidazo[2,1-b]thiazole.

This product is also prepared by the following alternative procedure.

(d) A suspension of 108.8 g. (0.4 mole) of p-anisoin and 60.8 g. (0.8 mole) of thiourea in 500 ml. of 1-hexanol was heated to reflux with stirring with continuous azeotropic water removal. A clear orange solution resulted which was refluxed for 2.5 hours and then allowed to cool to 25° C. The suspension was filtered, and the crystals washed with ether. The mother liquor deposited a second crop which was combined with the first, heated in ethanol, cooled and filtered to give 4,5-bis(p-anisyl)-2-mercaptoimidazole, m.p. 270° C.

A mixture of 4 g. (0.0128 mole) of the above prepared mercaptoimidazole, 2.4 g. (0.0128 mole) of 1,2-dibromoethane and 2.65 g. (0.0192 mole) of potassium carbonate in 50 ml. of sieve dried dimethylformamide was heated under nitrogen to reflux with magnetic stirring for 3 hours. After cooling, 550 ml. of water was added and the ph brought to 11 with 10% aqueous sodium hydroxide solution. The precipitate was filtered, washed with water and dissolved in methylene chloride. The organic phase was washed eight times with water, dried over potassium carbonate, filtered, decolorized twice with charcoal and filtered, and evaporated in vacuo. The residue was recrystallized from acetonitrile, chloroform-hexane, methylene chloride-hexane and aqueous methanol to give 5,6-bis(p-anisyl)-2,3-dihydroimidazo[2,1-b]thiazole.

EXAMPLE 2

Bromine (30 g.) was added dropwise to 40 g. of p,p'-dimethyldesoxybenzoin in 250 ml. of benzene at room temperature. After stirring for 20 minutes, the solvent was removed in vacuo and the resulting solid was dissolved in hexane-benzene, treated with activated charcoal, filtered and cooled to give p,p'-dimethyl-α-bromodesoxybenzoin, m.p. 96°–97° C.

Ten grams of p,p'-dimethyl-α-bromodesoxybenzoin and 3.4 g. of 2-amino-4,5-dihydrothiazole in 60 ml. of acetonitrile was stirred at room temperature for 24 hours. The resultant precipitate was removed by filtration, washed with ether, dried and recrystallized from ethanol to give 5,6-bis(p-tolyl)-2,3-dihydroimidazo[2,1-b]thiazole hydrobromide, m.p. 258°–260° C.

EXAMPLE 3

6.33 Grams (0.04 mole) of bromine was added dropwise to 10.0 g. (0.038 moles) of p,p-dichlorodesoxybenzoin in benzene (100 ml.) stirred at room temperature. After 25 minutes, the solvent was removed at reduced pressure. Crystallization of the residue from ethanol gave p,p'-dichloro-α-bromodesoxybenzoin.

A solution of 10.0 g. (0.03 mole) of the above prepared α-bromo-desoxybenzoin and 3.1 g. (0.03 mole) of 2-amino-4,5-dihydrothiazole in acetonitrile was stirred at room temperature for 4 days. The mixture was cooled and the precipitate removed by filtration. Recrystallization from methanol gave the hydrobromide of 5,6-bis(p-chlorophenyl)-2,3-dihydroimidazo[2,1-b]thiazole, m.p. 289°–290° C.

EXAMPLE 4

A mixture of 300 g. (1.39 moles) of p-bromophenylacetic acid and 663.8 g. (5.58 moles) of thionyl chloride was refluxed under nitrogen for 1 hour. The excess thionyl chloride was removed in vacuo. A stirred mixture of this residue, 436.5 g. (2.78 moles) of bromobenzene (distilled) and one liter of sieve dried methylene chloride, under nitrogen atmosphere, was treated portionwise with 222.4 g. (1.67 moles) of aluminum chloride. The mixture was refluxed for 75 minutes, allowed to cool to room temperature and added slowly to aqueous hydrochloric acid. Additional methylene chloride was added, and the organic layer was washed with dilute aqueous sodium carbonate, twice with water, dried over potassium carbonate and evaporated in vacuo. The residue was recrystallized from methylene chloride-hexane to give p,p'-dibromodesoxybenzoin, m.p. 131°–137° C.

To 52.2 g. (0.147 mole) of p,p'-dibromodesoxybenzoin in 500 ml. of benzene was added 23.56 g. (0.147 mole) of bromine dropwise. The solution was stirred for 1 hour and evaporated in vacuo. The material was recrystallized from benzene-hexane to give α,p,p'-tribromodesoxybenzoin.

A mixture of 22.21 g. (0.0507 mole) of α,p,p'-tribromodesoxybenzoin, 10.36 g. (0.101 mole) of 2-amino-4,5-dihydrothiazole and 21.02 g. (0.152 mole) of potassium carbonate was stirred for 3 days in 150 ml. of acetonitrile under nitrogen at room temperature. Filtration of this mixture gave a solid which was washed with water and air dried. Thirty-seven percent of this solid was stirred in 100 ml. of methanol under an inert atmosphere and 8.9 g. of a 45.1% solution of methanolic hydrogen chloride was added dropwise. The solution was heated to reflux for 30 minutes and then evaporated in vacuo. The residual solid was dissolved in hot methanol, treated with charcoal, filtered, treated with water, adjusted to pH 11 with aqueous sodium hydroxide, chilled and filtered to give 5,6-bis(p-bromophenyl)-2,3-dihydroimidazo[2,1-b]thiazole, m.p. 208°–210° C.

EXAMPLE 5

By the procedure of Example 1, using the following in place of desoxy-p-anisoin:
3'-methyl-2-(p-tolyl)acetophenone
2'-methyl-2-(p-tolyl)acetophenone
2'-methyl-2-(m-tolyl)acetophenone
4'-chloro-2-(o-chlorophenyl)acetophenone
4'-chloro-2-(p-methoxyphenyl)acetophenone the products are, respectively:
6-(m-tolyl)-5-(p-tolyl)-2,3-dihydroimidazo[2,1-b]thiazole
6-(o-tolyl)-5-(p-tolyl)-2,3-dihydroimidazo[2,1-b]thiazole
6-(o-tolyl)-5-(m-tolyl)-2,3-dihydroimidazo[2,1-b]thiazole
5-(o-chlorophenyl)-6-(p-chlorophenyl)-2,3-dihydroimidazo[2,1-b]thiazole
6-(p-chlorophenyl)-5-(p-anisyl)-2,3-dihydroimidazo[2,1-b]thiazole.

EXAMPLE 6

The following substituted benzoins:
p,p'-diisopropylbenzoin
m,m'-dibromobenzoin
m,m'-dichlorobenzoin
o,o'-dichlorobenzoin
were reduced by the procedure of Example 11 to give the corresponding desoxybenzoins.

Using these desoxybenzoins as starting materials in the procedure of Example 1(a) and the resulting bromodesoxybenzoins in the procedure of Example 1(c), the products are, respectively:
5,6-bis(p-isopropylphenyl)-2,3-dihydroimidazo[2,1-b]thiazole
5,6-bis(m-bromophenyl)-2,3-dihydroimidazo[2,1-b]thiazole
5,6-bis(m-chlorophenyl)-2,3-dihydroimidazo[2,1-b]thiazole
5,6-bis(o-chlorophenyl)-2,3-dihydroimidazo[2,1-b]thiazole.

EXAMPLE 7

11.2 Grams (0.07 mole) of bromine in benzene (65 ml.) was added dropwise to a benzene slurry (65 ml.) of 16.3 g. (0.07 mole) of p,p-difluorodesoxybenzoin stirred at 0° C. The solvent was then removed at reduced pressure to give p,p'-difluoro-α-bromodesoxybenzoin.

A slurry of 14.3 g. (0.07 mole) of p,p-difluoro-α-bromodesoxybenzoin, 11.2 g. (0.06 mole) of 2-amino-4,5-dihydrothiazole and 18.6 g. (0.12 mole) of sodium carbonate in acetonitrile (150 ml.) was stirred overnight at room temperature. The precipitate was removed by filtration and extracted with methylene chloride. The extract was then washed with water, dried over magnesium sulfate, filtered and the solvent removed at reduced pressure to give 6-hydroxy 5,6-bis(p-fluorophenyl)-2,3,5,6-tetrahydromidazo[2,1-b]thiazole, m.p. 159°–160° C. This was then dissolved in ethanol and ethereal hydrogen chloride added. The solution was cooled and the resulting crystals removed to give 5,6-bis(p-fluorophenyl)-2,3-dihydroimidazo[2,1-b]thiazole hydrochloride, m.p. 280°–282° C.

EXAMPLE 8

By the procedure of Example 11, p,p-diethylbenzoin is reduced with tin and hydrochloric acid to give p,p'-diethyldesoxybenzoin. Brominating this desoxybenzoin by the procedure of Example 1(a) gives p,p'-diethyl-α-bromodesoxybenzoin.

A mixture of p,p'-diethyl-α-bromodesoxybenzoin, 2-amino-4,5-dihydrothiazole, potassium carbonate and acetonitrile is stirred at room temperature for 72 hours. Working up as in Example 1(c) gives 5,6-bis(p-ethylphenyl)2,3-dihydroimidazo[2,1-b]thiazole.

By the same method, using as starting materials the following benzoins:
p,p-di-sec-butylbenzoin
p,p'-dipropoxybenzoin
the products are, respectively:
5,6 -bis(p-sec-butylphenyl)-2,3-dihydroimidazo[2,1-b]thiazole
5,6-bis(p-propoxyphenyl)-2,3-dihydroimidazo[2,1-b]thiazole.

EXAMPLE 9

To a solution of 5,6-bis(p-anisyl)-2,3-dihydroimidazo[2,1-b]thiazole in 3 parts methylene chloride and 1 part absolute ethanol is added a solution containing an equimolar amount of sulfuric acid dissolved in absolute ethanol. The mixture is stripped of solvent and the residue recrystallized from absolute ethanol-ether containing a small amount of added sulfuric acid to give 5,6-bis(p-anisyl)-2,3-dihydroimidazo[2,1-b]thiazole sulfate, m.p. 268°–273° C. (dec.).

EXAMPLE 10

To a solution of 5,6-bis(p-anisyl)-2,3-dihydroimidazo[2,1-b]thiazole in absolute ethanol is added a solution containing an equimolar amount of tartaric acid dissolved in ethanol. The mixture is stripped of solvent to give 5,6-bis(p-anisyl)-2,3-dihydroimidazo[2,1-b]thiazole tartrate, m.p. 193°–200° C.

By the procedure, using methanesulfonic acid in place of tartaric acid, the methanesulfonate salt is prepared.

In the same manner, using phosphoric acid, 5,6-bis(p-anisyl)-2,3-dihydroimidazo[2,1-b]thiazole phosphate is prepared.

EXAMPLE 11

The following are general procedures for the preparation of the benzoin starting materials in the procedures for preparing compounds of this invention.

The benzaldehyde (0.36 mole) was refluxed in 150 ml. of 1:1 ethanol-water mixture with potassium cyanide (0.07 mole) until progress of reaction was no longer evident, for example by thin layer chromatography or gas liquid phase chromatography. The reaction mixture was diluted with water to 400 ml. and was extracted with chloroform. The organic extract was washed with water, saturated brine, dried over magnesium sulfate, filtered and evaporated at reduced pressure to obtain the crude benzoin which was purified by distillation or recrystallization.

The benzoin (0.075 mole) was dissolved in 80 ml. of alcohol and 20 g. of tin (20 mesh) was added. The mixture was gently heated and a solution containing 28 ml. of concentrated hydrochloric acid, 0.8 g. of anhydrous cupric sulfate and 0.5 ml. of water was added. The reaction mixture was refluxed until thin layer chromatography no longer detected the presence of starting material. The granular tin was removed by filtration and the filtrate was evaporated to an oil which was diluted with water to 400 ml. and was extracted with chloroform. The organic extract was washed with 5% aqueous sodium carbonate solution (45 ml.×3), with water (45 ml.×2) and with brine; it was dried over anhydrous magnesium sulfate and evaporated to obtain desoxybenzoin.

EXAMPLE 12 p,p'-Diethoxydesoxybenzoin (5.2 g., 0.020 mole) was dissolved in 80 ml. carbon tetrachloride and an equivalent amount of bromine (1.0 ml.) was slowly added in 30 ml. of carbon tetrachloride. Whenever the reaction appeared to proceed slowly, it was accelerated by irradiation by a 275 W sunlamp. After bromine addition was complete, the solution was allowed to stir for an additional 30 minutes and the solvent was evaporated at reduced pressure to give p,p'-diethoxy-α-bromodesoxybenzoin.

By the procedure of Example 1, the above prepared bromodesoxybenzoin was reacted with 2-amino-4,5-dihydrothiazole and potassium carbonate in acetonitrile to give 5,6-bis(p-ethoxyphenyl)-2,3-dihydroimidazo[2,1-b]thiazole (sulfate, m.p. 214°–215° C.).

EXAMPLE 13 o-Anisoin was reduced to desoxy-o-anisoin by the procedure described in Example 11.

By the procedure of Example 12, desoxy-o-anisoin was brominated to give α-bromodesoxy-o-anisoin and this was reacted with 2-amino-4,5-dihydrothiazole by the procedure of Example 1(c) to give 5,6-bis(o-anisyl)-2,3-dihydroimidazo[2,1-b]thiazole (hydrobromide, m.p. 238°–240° C.).

By the same procedure, using m-anisoin, 5,6-bis(m-anisyl)-2,3-dihydroimidazo[2,1-b]thiazole was prepared (hydrobromide, m.p. 212°–213° C.).

EXAMPLE 14

The following benzoins (0.020 mole):
m,m'-dimethylbenzoin
m,m'-difluorobenzoin
bis(3-fluoro-4-methoxy)benzoin
bis(4-methoxy-3-methyl)benzoin
were mixed with thiourea (0.040 mole) and refluxed in 40 ml. of dimethylformamide for 2.5 hours. The hot reaction mixture was poured into ice water. The precipitate was filtered off and recrystallized from isopropanol to give, respectively:
4,5-bis(m-tolyl)-2-mercaptoimidazole
4,5-bis(m-fluorophenyl)-2-mercaptoimidazole
4,5-bis(3-fluoro-4-methoxyphenyl)-2-mercaptoimidazole
4,5-bis(4-methoxy-3-methylphenyl)-2-mercaptoimidazole.

The above prepared mercaptoimidazoles (0.007 mole) were dissolved in 50 ml. of dimethylformamide and 2-chloroethyl bromide (0.010 mole) was added. The solution was refluxed for 1.5 hour, allowed to cool, anhydrous potassium carbonate (0.010 mole) was added and the resulting mixture refluxed for 2 hours. The mixture was poured into ice water and the precipitate was filtered off and recrystallized to give:
5,6-bis(m-tolyl)-2,3-dihydroimidazo[2,1-b]thiazole, m.p. 118°–119° C.
5,6-bis(m-fluorophenyl)-2,3-dihydroimidazo[2,1-b]thiazole, m.p. 145.5°–146.5° C.
5,6-bis(3-fluoro-4-methoxyphenyl)-2,3-dihydroimidazo[2,1-b]thiazole, m.p. 185°–187° C.
5,6-bis(4-methoxy-3-methylphenyl)-2,3-dihydroimidazo[2,1-b]thiazole (perchlorate, m.p. 221°–222° C.).

EXAMPLE 15 p-Methoxyphenylacetic acid (38.15 g., 0.23 mole) was stirred in 200 ml. of thionyl chloride until hydrogen chloride evolution was no longer noticeable. The excess thionyl chloride was removed at reduced pressure and the residual acid chloride was distilled at 140°–50°/10 mm Hg. A methylene chloride (200 ml.) solution of the acid chloride was slowly added to 500 ml. benzene containing 100 g. of aluminum chloride. The reaction temperature was controlled by intermittent cooling in an ice bath. After overnight reaction at room temperature, the reaction mixture was slowly treated with 100 ml. of water and the organic layer was separated, washed with water and evaporated to an oil. The p'- methoxydesoxybenzoin was isolated by vacuum distillation at 150°–165° C./2.5 mm Hg.

The desoxybenzoin (0.020 mole) was dissolved in 80 ml. of carbon tetrachloride and an equivalent amount of bromine (1.0 ml.) was slowly added in 30 ml. of carbon tetrachloride. Whenever the reaction appeared to proceed slowly, it was accelerated by the irradiation with a sunlamp. After bromine addition was complete, the solution was stirred for an additional 30 minutes and the solvent was evaporated at reduced pressure to give p'-methoxy-α-bromodesoxybenzoin.

Reaction of the above prepared p'-methoxy-α-bromodesoxybenzoin with 2-amino-4,5-dihydrothiazole by the procedure of Example 1(c) giives 5-(p-anisyl)-6-phenyl-2,3-dihydroimidazo[2,1-b]thiazole (hydrobromide, m.p. 228°–231° C.).

EXAMPLE 16 p-Hydroxydesoxybenzoin (5.0 g., 0.023 mole) was dissolved in 5 N aqueous sodium carbonate solution (40 ml.). The solution was treated with 10 ml. of dimethylsulfate dropwise. The pH of the solution was monitored and kept above 9 by the addition of sodium carbonate as needed. The precipitate was filtered and recrystallized from methanol to give p-methoxydesoxybenzoin. By the procedure of Example 12, this desoxybenzoin was brominated and treated with 2-amino-4,5-dihydrothiazole to give 6-(p-anisyl)-5-phenyl-2,3-dihydroimidazo[2,1-b]thiazole (hydrobromide, m.p. 273°–274° C.).

EXAMPLE 17

A solution of 50.0 g. (0.199 mole) of boron tribromide in 200 ml. of sieve dried methylene chloride was added dropwise to a mixture of 39.92 g. (0.118 mole) of 5,6-bis(p-anisyl)-2,3-dihydroimidazo[2,1-b]thiazole and 500 ml. of dry methylene chloride at −60° C. under nitrogen with stirring. After stirring the mixture overnight at room temperature, 250 ml. of water was added dropwise and the reaction mixture was poured into 500 ml. of water. The crude product was filtered off and recrystallized from methanolether to give 5,6-bis(p-hydroxyphenyl)-2,3-dihydroimidazo[2,1-b]thiazole hydrobromide, m.p. 341°–350° C. (dec).

EXAMPLE 18

2.5 Grams (8 mmole) of 5,6-bis(p-hydroxyphenyl)-2,3-dihydroimidazo[2,1-b]thiazole was dissolved in 25 ml. pyridine and 5 ml. acetic anhydride was added. The solution was stirred overnight at ambient temperature and was poured into a mixture of ice and 25 ml. dilute hydrochloric acid. The precipitate was filtered after about 25–30 minutes and was chromatographed on silica eluting with ether to give 5,6-bis(p-acetoxyphenyl)-2,3-dihydroimidazo[2,1-b]thiazole, m.p. 172°–173° C.

EXAMPLE 19

Treatment of p,p'-dihydroxydesoxybenzoin (5.9 g.) with n-butyl iodide (6.5 ml.) and potassium carbonate (7.5 g.) followed by sequential treatment with 2.1 g. of sodium hydride and 5.0 ml. of iodide afforded bis(p-butoxy)desoxybenzoin which was purified by recrystallization from methanol.

The above prepared desoxybenzoin was brominated by the procedure of Example 12 and the resulting p,p-dibutoxy-α-bromodesoxybenzoin was reacted with 2-amino-4,5-dihydrothiazole and potassium carbonate in acetonitrile by the procedure of Example 1 to give 5,6-bis(p-butoxyphenyl)-2,3-dihydroimidazo[2,1-b]thiazole (sulfate, m.p. 149°–151° C.).

EXAMPLE 20

A solution of 10.0 g. (0.03 mole) of 5,6-bis-(p-anisyl)-2,3-dihydroimidazole[2,1-b]thiazole in 294 ml. of methanol and 147 ml. of methylene chloride was added dropwise with stirring to 60 ml. of an aqueous solution of 7.1 g. (0.03 mole) sodium periodate at 0° C. The mixture was then stirred for several days at room temperature. The mixture was treated with an equal volume of water and extracted several times with methylene chloride. The extract was concentrated and chromatographed on an alumina dry column and developed with a 1:1 (vol.) mixture of chloroform and ethyl acetate. The product was extracted from the alumina with methanol and the methanol solution concentrated in vacuo. The residue was dissolved in methylene chloride, dried over magnesium sulfate, filtered and the filtrate evaporated to give 5,6-bis(p-anisyl)-2,3-dihydroimidazo[2,1-b]thiazol-1-oxide, m.p. 190°–191° C.

EXAMPLE 21

To a solution of 8.0 g. (0.0238 mole) 5,6-bis-(p-anisyl)-2,3-dihydroimidazo[2,1-b]thiazole in 80 ml. of methylene chloride and 80 ml. of ethanol was added dropwise with stirring a solution of 18.4 g. of 85% (0.091 mole) m-chloroperbenzoic acid in 160 ml. of ethanol. The mixture was stirred at 47° C. for 2 hours, then filtered. The solid material obtained was washed with ethanol and purified by dry column chromatography on alumina eluted with tetrahydrofuran, then recrystallized from acetonitrile to give 5,6-bis(p-anisyl)-2,3-dihydroimidazo[2,1-b]thiazole-1,1-dioxide, m.p. 231°–232° C.

EXAMPLE 22

A stirred mixture of 90 g. (0.276 mole) of p,p'-diacetamidobenzoin and 42 g. (0.553 mole) of thiourea in 700 ml. of hexanol was refluxed with continuous azeotropic water removal for 3.5 hours under nitrogen. After cooling to room temperature overnight, the precipitate was filtered off, washed with petroleum ether, suspended in cold methanol, filtered again, washed with methanol and petroleum ether and air dried to give 4,5-bis(p-acetamidophenyl)-2-mercaptoimidazole, m.p. 368°–382° C. (dec.).

A mixture of 10.0 g. (0.027 mole) of 4,5-bis-(p-acetamidophenyl)-2-mercaptoimidazole and 4.9 g. (0.034 mole) of 2-chloroethyl bromide in 80 ml. of sieve dried dimethylformamide was refluxed with stirring under nitrogen for 75 minutes. Potassium carbonate (3.8 g., 0.027 mole) was added and the suspension was refluxed for 2 hours, then allowed to cool to room temperature and poured into 650 ml. of water. The gum which formed was filtered off and crystallized from 50 ml. of hot methanol. The crystals were washed with cold methanol and ether and air dried to give 5,6-bis(p-acetamidophenyl)-2,3-dihydroimidazo[2,1-b]thiazole, m.p. 285°–290° C.

EXAMPLE 23

A suspension of 25 g. (0.064 mole) of 5,6-bis-(p-acetamidophenyl)-2,3-dihydroimidazo[2,1-b]thiazole, prepared as in Example 22, in 250 ml. of 6 N hydrochloric acid was refluxed with stirring under nitrogen for 1.75 hours. This solution was chilled, made alkaline with 10% aqueous sodium hydroxide and filtered. The precipitate was washed with a small amount of acetonitrile and recrystallized from acetonitrile with charcoal to give 5,6-bis(p-aminophenyl)-2,3-dihydroimidazo[2,1-b]thiazole, m.p. 205°–206.5° C.

EXAMPLE 24

A stirred mixture of 3.2 g. (0.0104 mole) of 5,6-bis(p-aminophenyl)-2,3-dihydroimidazo[2,1-b]thiazole, 4.8 g. (0.026 mole) of pivalic anhydride and 3.18 g. (0.031 mole) of pivalic acid was refluxed at 195°–210° C. under nitrogen for 75 minutes. After cooling to room temperature, the mixture was dissolved in hot chloroform. This solution was washed with 5% aqueous sodium carbonate and water, then dried over anhydrous magnesium sulfate, filtered and evaporated in vacuo. The residue was recrystallized from methanol-ether and then from chloroform to give 5,6-bis(p-pivalamidophenyl)-2,3-dihydroimidazo[2,1-b]thiazole, m.p. 210°–215° C.

EXAMPLE 25

A mixture of 10.0 g. (0.0256 mole) of 5,6-bis-(p-hydroxyphenyl)-2,3-dihydroimidazo[2,1-b]thiazole hydrobromide, 7.42 g. (0.0614 mole) of allyl bromide and 3.69 g. of sodium hydride (50% dispersion in oil, 0.0768 mole) in 100 ml. of sieve dried dimethylformamide was heated to 60°–75° C. for one hour with stirring under nitrogen. The suspension was poured into 500 ml. of water. The mixture was adjusted to pH 11 with 10% aqueous sodium hydroxide and extracted three times with methylene chloride. The organic solution was washed with water, dried over potassium carbonate, evaporated and the residue triturated with petroleum ether to give a crystalline solid. This solid was chromatographed on alumina eluting with a mixture of ether, methylene chloride, petroleum ether (1:1:1) and the major fraction concentrated in vacuo. The residue was recrystallized from methylene chloride and hexane to give 5,6-bis(p-allyloxyphenyl)-2,3-dihydroimidazo[2,1-b]thiazole, m.p. 135°–137.5° C.

EXAMPLE 26

A stirred solution of 52.6 g. (0.312 mole) of trifluoromethanesulfonyl chloride (freshly distilled) in 65 ml. of methylene chloride (distilled from calcium hydride) at −58° C. was treated dropwise with a mixture of 32.6 g. (0.322 mole) of triethylamine (dried over potassium hydroxide) and 32.2 g. (0.322 mole) of trifluoroethanol (freshly distilled) under nitrogen and allowed to come to room temperature overnight. The methylene chloride solution was washed once with 5% hydrochloric acid and three times with water, dried over magnesium sulfate and distilled. The 2,2,2-trifluoroethyl trifluoromethanesulfonate was collected, b.p. 92°–93° C.

To a stirred suspension of 6.14 g. of sodium hydride [50% dispersion in oil, (0.128 mole)] in 150 ml. of tetrahydrofuran (distilled from lithium aluminum hydride) at 0° C. under nitrogen was added 10.0 g. (0.0256 mole) of 5,6-bis(p-hydroxyphenyl)-2,3-dihydroimidazo[2,1-b]thiazole hydrobromide. After 30 minutes, 17.82 g. (0.0768 mole) of 2,2,2-trifluoroethyl trifluoromethanesulfonate was added dropwise, maintaining the temperature below 0° C. After stirring overnight at room temperature, the suspension was added portionwise to 500 ml. of ice water under nitrogen and extracted three times with methylene chloride. The organic layer was washed with water, dried over potassium carbonate and concentrated in vacuo. The residue was recrystallized from methylene chloride-hexane to give 5,6-bis[p-(2,2,2-trifluoroethoxy)phenyl]-2,3-dihydroimidazo[2,1-b]thiazole, m.p. 163°–164° C.

EXAMPLE 27

A solution of 15 g. (0.042 mole) of p,p-bis-(trifluoromethyl)-α-phenylcinnamic acid and thionyl chloride (60 ml.) in benzene (100 ml.) was refluxed for 2 hours. The volatile materials were removed at reduced pressure and the residue dissolved in acetone (50 ml.). The acetone solution was added dropwise, with stirring, to a solution of 2.7 g. (0.042 mole) of sodium azide in water (20 ml.) at 10°–15° C. After one hour, the cold solution was extracted with benzene, the benzene extract washed with water and dried over magnesium sulfate. The mixture was filtered and the acid azide solution refluxed for 30 minutes. The benzene was removed at reduced pressure and the residual acid isocyanate treated with 75 ml. of a 2:1 acetic acid-water solution at 65° C. for one hour. The resulting precipitate was collected, washed with water and recrystallized from ethanol to give p,p'-di(trifluoromethyl)desoxybenzoin, m.p. 113°–115° C.

A solution of 6.2 g. (0.039 mole) of bromine in benzene (20 ml.) was added dropwise to 8.3 g. (0.025 mole) of p,p'-di(trifluoromethyl)desoxybenzoin in benzene (100 ml.). An infra red lamp was used initially to induce bromination. After 20 minutes, the solvent was removed at reduced pressure to give p,p'-di(trifluoromethyl)-α-bromodesoxybenzoin, m.p. 59°–60° C. (from hexane).

The bromodesoxybenzoin was dissolved in acetonitrile (100 ml.), 2.6 g. (0.025 mole) of 2-amino-4,5-dihydrothiazole and 7.0 g. (0.05 mole) of potassium carbonate were added and the mixture was stirred at room temperature for 60 hours. The solvent was removed at reduced pressure and the residue dissolved in chloroform (300 ml.). The chloroform solution was washed with water, dried over potassium carbonate and the solvent removed at reduced pressure to give 6-hydroxy-5,6-bis(p-trifluoromethylphenyl)-2,3,5,6-tetrahydroimidazole[2,1-b]thiazole, m.p. 175°–177° C.

A solution of 2.9 g. (6.7 mmoles) of 6-hydroxy-5,6-bis(p-trifluoromethylphenyl)-2,3,5,6-tetrahydroimidazo[2,1-b]thiazole in toluene (200 ml.) was refluxed with continuous azeotropic distillation of the resulting water. The solvent was removed at reduced pressure and the residue dissolved in ethanol and treated with 48% aqueous hydrobromic acid. The solution was evaporated to dryness and treated with 40 ml. of hot benzene. Filtration of the solid and drying gave 5,6-bis(4-trifluoromethylphenyl)-2,3-dihydroimidazo[2,1-b]thiazole hydrobromide, m.p. 314°–315° C.

EXAMPLE 28

42.8 Grams (0.32 moles) of aluminum chloride was added in portions to a solution of 45.9 g. (0.2 mole) of homoveratryl chloride and benzene (25 ml.) in methylene chloride (300 ml.). The mixture was then refluxed 1.5 hours, cooled and poured into a mixture comprised of 300 ml. of ice, 100 ml. of water and 225 ml. of concentrated hydrochloric acid. The organic phase was separated and the aqueous layer extracted with chloroform. The combined organic layers were washed with water, dried over magnesium sulfate, filtered and the solvent removed at reduced pressure to give an oil. Chromatography (2×) over alumina (ethyl acetate) followed by treatment with ether gave 3',4'-dimethoxydesoxybenzoin, m.p. 80°-81° C.

15.4 Grams (0.06 mole) of 3',4'-dimethoxydesoxybenzoin in 50 ml. of dimethylformamide was added to a solution of 7.8 g. (0.07 mole) of trimethylsilyl chloride and 14.6 g. (0.14 mole) of triethylamine in dimethylformamide (25 ml.). The mixture was refluxed for 11 hours, cooled and diluted with petroleum ether (200 ml.). This was then extracted successively with 5% sodium bicarbonate, 1.5 M hydrochloric acid and 5% sodium bicarbonate and dried over magnesium sulfate. After filtering, the solvent was removed at reduced pressure to give the enol ether. This was dissolved in carbon tetrachloride (40 ml.) and cooled to 0° C. 5.8 Grams (0.036 mole) of bromine in carbon tetrachloride (40 ml.) was then added dropwise and the volatile materials removed at reduced pressure to give as the residue 3',4'-dimethoxy-α-bromodesoxybenzoin. This was dissolved in acetonitrile (40 ml.) and 0.5 g. (0.09 mole) of sodium carbonate and 4.6 g. (0.045 mole) of 2-amino-4,5-dihyrothiazole were added. After stirring overnight, the resulting yellow solid was collected and washed with water. It was dissolved in a minimum of dimethylformamide, cooled, filtered and the crystals washed with ether to give 5-(3,4-dimethoxyphenyl)-6-phenyl-2,3-dihydroimidazo[2,1-b]thiazole, m.p. 176°-177.5° C. The free base was dissolved in ethanol and treated with 48% aqueous hydrobromic acid to give 5-(3,4-dimethoxyphenyl)-6-phenyl-2,3-dihydroimidazo[2,1-b]thiazole hydrobromide, m.p. 244°-245° C.

EXAMPLE 29

A solution of 6.7 g. (0.02 mole) of 3,4-dimethoxy-α-bromodesoxybenzoin and 9.2 g. (0.09 mole) of 2-amino-4,5-dihydrothiazole in acetonitrile (75 ml.) was stirred at room temperature for 24 hours. The solvent was removed at reduced pressure. The residue was dissolved in methanol and 48% aqueous hydrobromic acid added to give, after cooling, 5-phenyl-6-(3,4-dimethoxyphenyl)-2,3-dihydroimidazo[2,1-b]thiazole hydrobromide, m.p. 221°-223° C.

EXAMPLE 30

A hexanol solution (300 ml.) of 15 g. (0.2 mole) of thiourea and 29.3 g. (0.1 mole) of p,p'-di(methylthio)-benzoin was refluxed for 3 hours with continuous azeotropic water removal. The solution was then cooled to 0° C. and the resulting yellow crystals removed by filtration, washed with ethanol and air-dried to give 4,5-bis(p-methylthiophenyl)-2-mercaptoimidazole, m.p. 280° C.

A mixture of 19.5 g. (0.06 mole) of 4,5-bis-(p-methylthiophenyl)-2-mercaptoimidazole, 10.7 g. (0.06 mole) of 1,2-dibromoethane and 7.9 g. (0.06 mole) of potassium carbonate in dimethylformamide (250 ml.) was refluxed for 3 hours. The mixture was then poured into 1 liter of ice-water and the yellow precipitate collected and washed with water. This material was then dissolved in chloroform, dried over magnesium sulfate, filtered and the solvent removed at reduced pressure. The residue was then treated with chloroform-ether and the white crystals of 5,6-bis(p-methylthiophenyl)-2,3-dihydroimidazo[2,1-b]thiazole collected. This was then dissolved in methanol and treated with aqueous hydrobromic acid. Filtering and recrystallizing from methanol gave 5,6-bis(p-methylthiophenyl)-2,3-dihydroimidazo[2,1-b]thiazole hydrobromide, m.p. 270° C.

EXAMPLE 31

A hexanol solution (170 ml.) of 10.9 g. (0.036 mole) of piperoin and 5.5 g. (0.072 mole) of thiourea was refluxed for 4 hours, with continuous azeotropic water removal. The mixture was cooled to 0° C. and the solid collected, washed with ether and dried. Recrystallization from dimethylformamide gave 4,5-bis(3,4-methylenedioxyphenyl)-2-mercaptoimidazole, m.p. 282°-283° C.

A slurry of 3.5 g. (0.01 mole) of 4,5-bis(3,4-methylenedioxyphenyl)-2-mercaptoimidazole, 2.0 g. (0.01 mole) of 1,2-dibromoethane and 2 g. (0.014 mole) of potassium carbonate in dimethylformamide (45 ml.) was refluxed for 2.5 hours and then poured into 500 ml. of ice water. The precipitate was collected, washed with water and dried. Chromatography (alumina/chloroform) gave 5,6-bis(3,4-methylenedioxyphenyl)-2,3-dihyroimidazo[2,1-b]thiazole. This was dissolved in methanol and treated with aqueous hydrobromic acid. The solvent was removed and the residue recrystallized from methanol to give 5,6-bis(3,4-methylenedioxyphenyl)-2,3-dihydroimidazo[2,1-b]thiazole hydrobromide, m.p. 278°-280° C.

EXAMPLE 32

A stirred mixture of 18.6 g. (0.047 mole) of 5,6-bis(p-acetamidophenyl)-2,3-dihydroimidazo[2.1-b]thiazole in 185 ml. of sieve dried dimethylformamide at −10° C. under a nitrogen atmosphere was treated with 6.8 g. of sodium hydride (50% oil dispersion, 0.142 mole) and allowed to warm. After one hour at 25° C., the solution was cooled to 5° C., a solution of 11.4 g. (0.105 mole) of bromoethane in 10 ml. of dry dimethylformamide was added, and the mixture stirred at 5° C. for one hour. The mixture was allowed to warm to room temperature, stirred two hours and quenched by dropwise addition of this mixture to 1 liter of ice water with stirring under nitrogen. The resulting suspension was extracted with methylene chloride (3×250 ml.) and the organic phase was washed with water, dried over magnesium sulfate, filtered and evaporated in vacuo. The residue was chromatographed on alumina eluting with ethyl acetate and chloroform (2:1). The solvent was evaporated in vacuo and the material recrystallized from ethyl acetate to give 5,6-bis(p-N-ethyl-acetamidophenyl)-2,3-dihydroimidazo[2,1-b]thiazole hemihydrate, m.p. 170.5°-171.5° C.

EXAMPLE 33

A mixture of 5.4 g. (0.012 mole) of 5,6-bis(p-N-ethyl-acetamidophenyl)-2,3-dihydroimidazo[2,1-b]thiazole hemihydrate and 80 ml. of 6 N aqueous hydrochloric acid was refluxed under nitrogen with stirring for 3 hours, cooled and made alkaline with a 10% solution of sodium hydroxide. The mixture was extracted with methylene chloride and the organic phase dried over anhydrous potassium carbonate, filtered and evaporated in vacuo to give 5,6-bis(p-N-ethylaminophenyl)-2,3-dihydroimidazo[2,1-b]thiazole.

A stirred solution of 3.64 g. (0.01 mole) of 5,6-bis(p-N-ethylaminophenyl)-2,3-dihydroimidazo[2,1-b]thiazole, 20 ml. of methanol and 2.84 g. (0.02 mole) of iodomethane is heated in a sealed vessel at 100° C. After 24 hours, the solvent is evaporated in vacuo and the residue treated with 10% aqueous sodium hydroxide solution. The mixture is extracted with methylene chloride and the organic phase dried over anhydrous potassium carbonate, filtered and evaporated in vacuo. The residue is chromatographed on alumina and eluted with chloroform and methylene chloride (1:1) to give, after evaporation of the solvent in vacuo, 5,6-bis(p-N-methyl-N-ethylaminophenyl)2,3-dihydroimidazo[2,1-b]thiazole.

EXAMPLE 34

A chloroform solution (400 ml.) of 42 g. (85%, 35.7 g., 0.21 mole) of meta-chloroperbenzoic acid was added dropwise to a slurry of 30.4 g. (0.1 mole) of p,p'-di(methylthio)benzoin in chloroform (500 ml.) kept at 0° C. Upon completion of the addition, the mixture was allowed to warm to room temperature and filtered. The solution was washed with 5% aqueous sodium carbonate (3×100 ml.), dried over magnesium sulfate, filtered and the solvent removed at reduced pressure to give p,p'-di(methylsulfinyl)benzoin.

A hexanol solution (150 ml.) of 9.0 g. (0.12 mole) of thiourea and 20 g. (0.06 mole) of p,p'-di(methylsulfinyl)benzoin was refluxed for 3 hours with continuous azeotropic water removal. The solution was cooled and the precipitate removed by filtration, washed with ethanol, then ether and air-dried. Recrystallization from a minimum of hot methanol gave 4,5-bis(p-methylsulfinylphenyl)-2-mercaptoimidazole, m.p. 261°–262° C.

A mineral oil suspension (3 g.) of 0.64 g. (15.9 mmoles) of potassium hydride was covered with anhydrous dimethylformamide (20 ml.) and cooled with stirring to 0° C. A solution of 3.0 g. (7.9 mmoles) of 4,5-bis(p-methylsulfinylphenyl)-2-mercaptoimidazole in dimethylformamide (20 ml.) was added followed, after 15 minutes, by the addition of 1.5 g. (7.9 mmole) of 1,2-dibromoethane in 10 ml. of dimethylformamide. The mixture was kept cold overnight, warmed to room temperature and poured into 600 ml. of ice-water. The resulting mixture was extracted with methylene chloride (4×50 ml.) and the combined extracts washed with water (2×100 ml.), dried over magnesium sulfate, filtered and the solvent removed at reduced pressure. Dry column chromatography (alumina, chloroform) gave 5,6-bis(p-methylsulfinylphenyl)-2,3-dihydroimidazole[2,1-b]thiazole.

EXAMPLE 35

| Ingredients | Amounts |
| --- | --- |
| 5,6-bis(p-anisyl)-2,3-dihydroimidazo[2,1-b]thiazole | 50 mg. |
| magnesium stearate | 5 mg. |
| lactose | 100 mg. |

The above ingredients are screened, mixed and filled into a hard gelatin capsule.

EXAMPLE 36

| Ingredients | Amounts |
| --- | --- |
| 5,6-bis(p-anisyl)-2,3-dihydroimidazo[2,1-b]thiazole | 100 mg. |
| calcium sulfate dihydrate | 150 mg. |
| sucrose | 20 mg |
| starch | 10 mg. |
| talc | 5 mg. |
| stearic acid | 3 mg. |

The sucrose, calcium sulfate dihydrate and 5,6-bis(p-anisyl)-2,3-dihydroimidazo[2,1-b]thiazole are mixed and granulated with 10% gelatin solution. The wet granules are screened, dried, mixed with the starch, talc and stearic acid, screened and compressed into a tablet.

EXAMPLE 37

| Ingredients | Amounts |
| --- | --- |
| 5,6-bis(p-anisyl)-2,3-dihydroimidazo[2,1-b]thiazole sulfate | 50 mg. |
| magnesium stearate | 5 mg. |
| lactose | 75 mg. |

The above ingredients are screened, mixed and filled into a hard gelatin capsule.

Similarly, the other compounds of Formula I may be formulated into pharmaceutical compositions by the procedures of Examples 35–37.

These pharmaceutical compositions are administered orally to a subject in need of antiarthric activity within the dose ranges given hereabove.

What is claimed is:

1. A compound of the formula:

<chemical structure with $R_1$, $R_2$, N, S, $(O)_n$> in which:
$R_1$ and $R_2$, being the same, are phenyl substituted by one lower alkylsulfinyl, 2,2,2-trifluoroethoxy or lower alkanoyloxy; and
n is 0, 1 or 2,
or a pharmaceutically acceptable acid addition salt thereof, said lower alkyl groups having 1–4 carbon atoms.

2. A pharmaceutical composition having antiarthritic activity, in dosage unit form, comprising a pharmaceutical carrier and a compound of claim 1.

3. A method of producing antiarthritic activity which comprises administering internally to an animal a compound of claim 1.

4. A compound of claim 1, said compound being 5,6-bis(p-methylsulfinylphenyl)-2,3-dihydroimidazo[2,1-b]thiazole.

5. A compound of claim 1, said compound being 5,6-bis(p-acetoxyphenyl)-2,3-dihydroimidazo[2,1-b]thiazole.

6. A compound of claim 1, said compound being 5,6-bis[p-(2,2,2-trifluoroethoxy)phenyl]-2,3-dihydroimidazo[2,1-b]thiazole.

* * * * *